United States Patent
Dunfee et al.

[11] Patent Number: 6,077,713
[45] Date of Patent: Jun. 20, 2000

[54] METHOD AND APPARATUS FOR EXTRACTING LIQUID SAMPLES FROM A CLOSED CONTAINER

[75] Inventors: William David Dunfee, New Castle, Del.; Edward Stephen Kaminski, North East, Md.; John Charles Mazza, Newark, Del.; Kerry Lynn Miller, Elkton, Md.; Jeffery Kenneth Parmer, Newark, Del.; Paul John Zuk, Lincoln University, Pa.

[73] Assignee: Dade Behring Inc., Deerfield, Ill.

[21] Appl. No.: 09/108,018

[22] Filed: Jun. 30, 1998

[51] Int. Cl.[7] .................................................. G01N 35/10
[52] U.S. Cl. ........................... 436/180; 436/43; 422/63; 422/81; 422/100; 422/103; 422/104; 422/110; 73/864.01; 73/864.24; 222/1; 222/61; 222/83
[58] Field of Search .................................. 422/63, 81, 100, 422/103, 104, 105, 110; 436/43, 54, 180; 73/864.01, 864.24; 222/1, 61, 83, 83.5, 400.7

[56] References Cited

U.S. PATENT DOCUMENTS

| | | |
|---|---|---|
| 4,477,578 | 10/1984 | Miles, et al. . |
| 4,713,974 | 12/1987 | Stone ..................................... 73/864.23 |
| 4,794,085 | 12/1988 | Jessop et al. ....................... 436/864.15 |
| 4,893,515 | 1/1990 | Uchida ................................. 73/864.34 |
| 4,926,701 | 5/1990 | Tompkins ................................. 73/7.1 |
| 4,951,512 | 8/1990 | Mazza et al. ....................... 73/861.23 |
| 4,986,138 | 1/1991 | Spencer ................................ 73/864.34 |
| 5,163,582 | 11/1992 | Godolphin et al. ........................ 222/1 |
| 5,289,451 | 2/1994 | De Silva et al. ...................... 422/68.1 |
| 5,413,246 | 5/1995 | Godolphin et al. ........................ 222/1 |
| 5,431,067 | 7/1995 | Anderson et al. ................... 73/863.86 |
| 5,463,895 | 11/1995 | Brentz .................................... 73/61.71 |
| 5,499,545 | 3/1996 | Kimura et al. ...................... 73/864.18 |
| 5,503,036 | 4/1996 | Nguyen et al. ..................... 73/864.34 |
| 5,525,298 | 6/1996 | Anami . |

FOREIGN PATENT DOCUMENTS 0 747 689 A2   12/1996   European Pat. Off. .

*Primary Examiner*—Long V. Le
*Attorney, Agent, or Firm*—Leland K. Jordan

[57] ABSTRACT

Extracting a quantity of liquid from a closed container by driving a cannula having a passage the length of the cannula and a groove a partial length of the cannula through the closure of the container until the groove establishes communication between a pressurized chamber and the container, thereby forcing liquid from the tube through the passage.

19 Claims, 6 Drawing Sheets

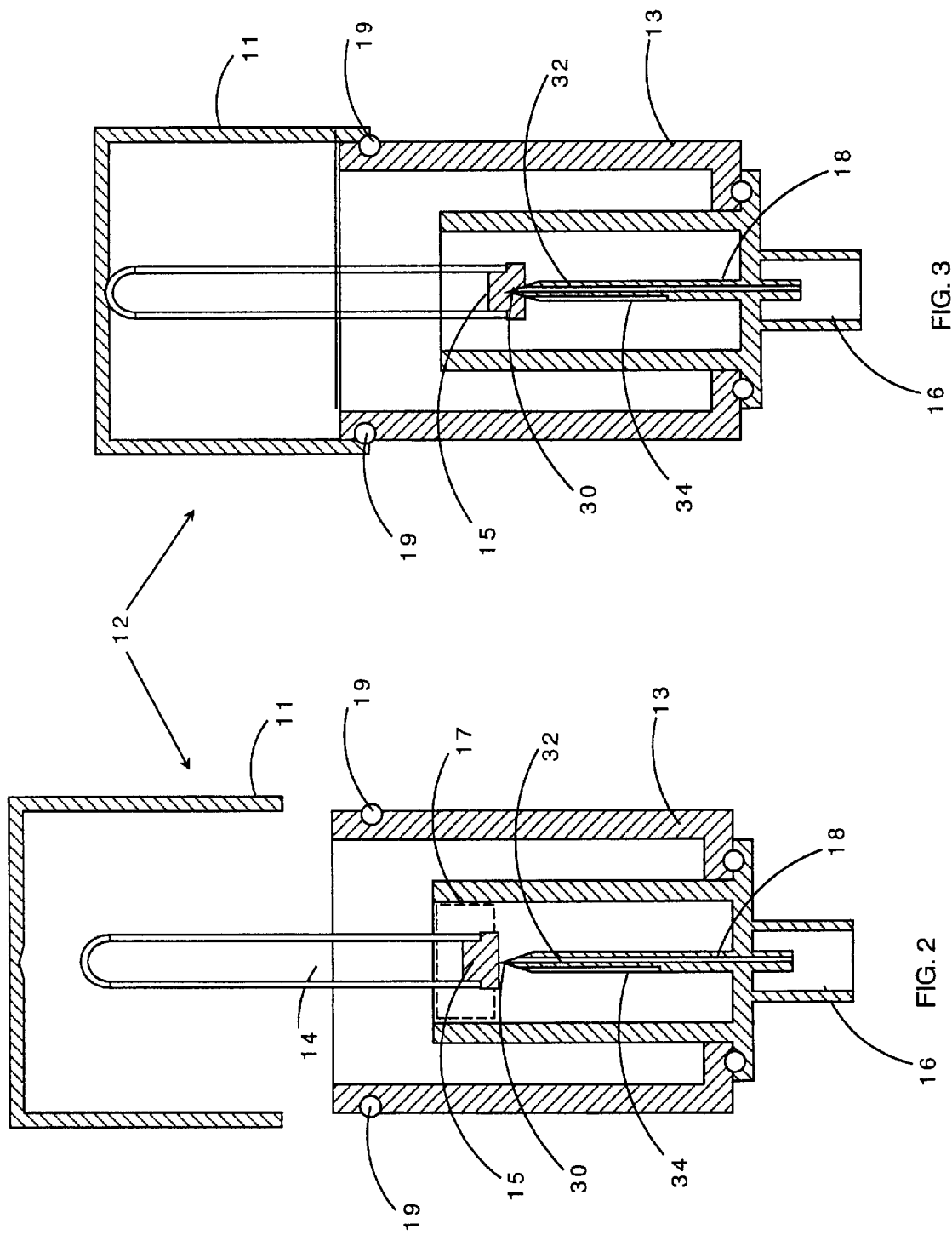

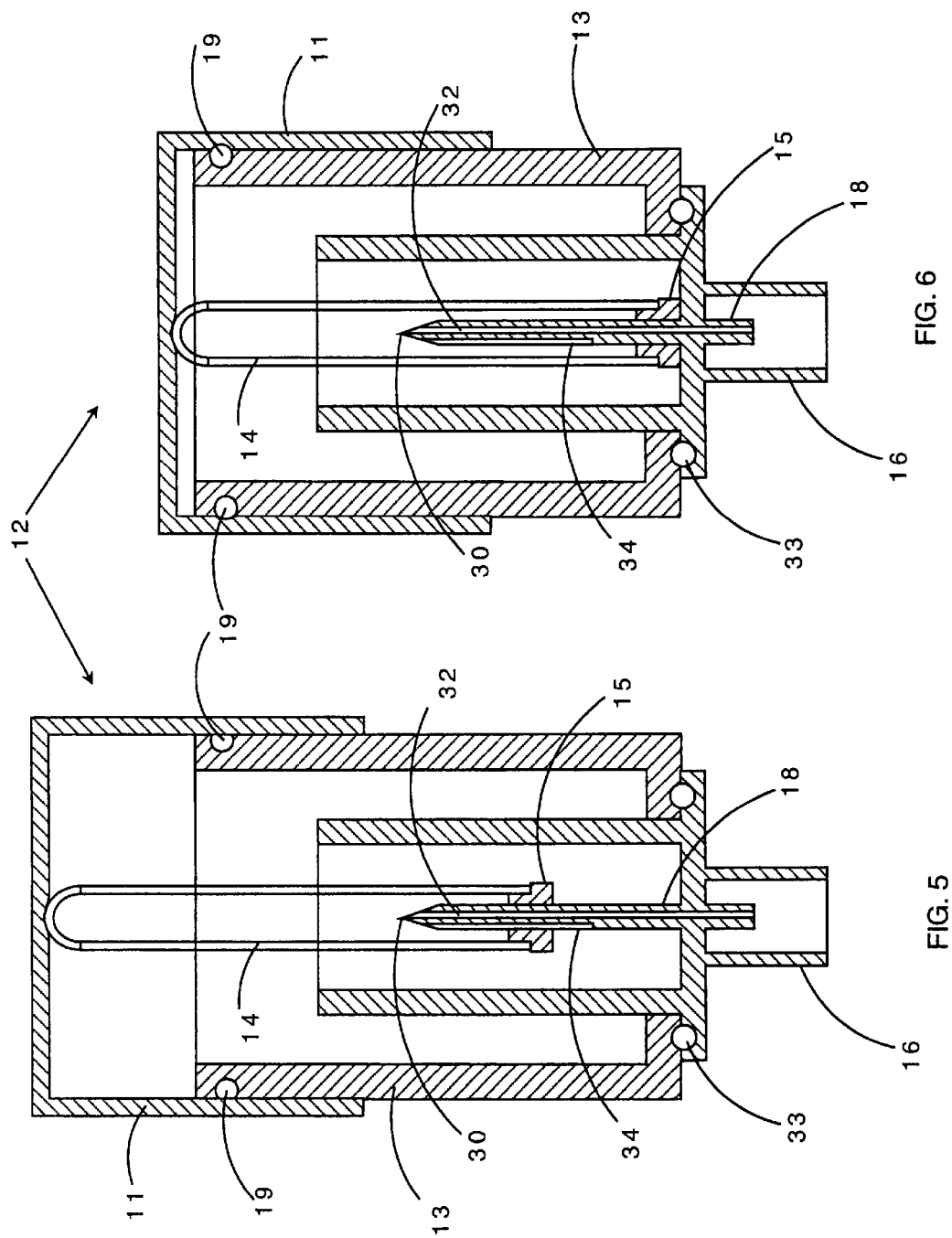

METHOD AND APPARATUS FOR EXTRACTING LIQUID SAMPLES FROM A CLOSED CONTAINER

BACKGROUND OF THE INVENTION

1. Field of the Invention

The present invention relates to an automated apparatus for extracting liquid samples, particularly biological fluids such as urine, blood serum, plasma, cerebrospinal fluid and the like, from a container. In particular, the present invention provides an improved method to automatically extract a desired amount of liquid sample from a closed container in preparation for clinical diagnosis.

2. Description of the Related Art

Clinical laboratories are routinely required to remove all or a portion of liquid samples from collection containers and a number of automated sampling systems have been produced to assist this operation. Generally, these systems receive sample containers, remove a predetermined quantity of sample from each container at a first location, and transfer the removed sample to a second location for analysis. The sample containers usually used with these systems are open-top vials or tubes transported in the system on carousels, racks or linear transports and then transferred between such devices with mechanical pusharms or other similar mechanisms.

Using open sample containers in an automatic sampling system presents a number of problems. First, the various forces which move the containers through the system cause spills and contamination. Second, open sample containers expose an operator to any harmful substances disposed in the containers. Finally, because open containers require special care, the cost of operation increases.

To avoid these problems, samples to be tested in automated clinical analysis systems are often collected in evacuated glass tubes closed with rubber stoppers and sealed with a vacuum. The sample displaces part of the vacuum; but some vacuum may remain. Removal of the stopper may result in the formation of aerosol particles. Consequently, when an operator removes the stopper before placing the container in the automated system, the aerosol spray may expose the operator to any harmful substances contained in the sample. In addition, removal of the stopper manually by the operator increases the cost of operation and decreases the efficiency and reliability of an automated system.

One solution to these problems is to present a closed container containing the sample to be analyzed to the automated analysis system and to employ an automated sampling system adapted to extract a known amount of liquid sample through the stopper of a closed tube or vial. To do so, available sampling system include an arrangement of needles, purge mechanisms, gas pressurization and other complex techniques to take samples from sealed sample containers. In addition to requirements placed on these sampling systems to remove at least a predetermined amount of liquid, concerns remain over the quality of the extracted sample, so that it be free of disruptive nonhomogenities like clots or bubbles.

U.S. Pat. No. 4,794,085 describes an apparatus and a method which permit the detection of penetration of liquid by an apertured container used for aspirating and dispensing the liquid. The apparatus has control means for advancing the container an increment of the maximum possible distance to the liquid, means to generate a pressure differential within the dispensing container that is sufficient to generate a signal that is indicative of whether the container aperture is closed by the liquid, and devices to detect and signal the pressure produced within the container by such a pressure differential, and to compare the signaled pressure against a reference U.S. Pat. No. 4,926,701 describes a pipetting device comprising a probe for dipping into a reservoir, reaction vessel or the like, a metering pump connected to the probe and a shutoff valve disposed between the probe and the pump are provided. In the intake phase of the pump with the valve open, first air and then a predetermined quantity of liquid is taken in. For at least some of the delivery phase of the pump the valve is in the closed state so that a pressure builds up in the pump. At the end of the delivery phase the valve opens whereby due to the high pressure any adhering liquid particles are expelled.

U.S. Pat. No. 4,951,512 provides for providing access to a sealed container which temporarily provides an opening in the closures of the containers, and either removes contents, senses properties of the contents, or dispenses material into the container. A lift assembly moves each sample container upward against a puncture tube to produce an opening in the closure of the container. The system takes a sample through this opening or inserts a probe through the opening to measure the properties of the sample.

U.S. Pat. No. 5,163,582 covers an apparatus and method for dispensing a predetermined volume of liquid from a closed, liquid-containing blood collection tube is described. The apparatus includes a dual conduit providing a passageway for liquid to be dispensed from a closed blood collection tube and a gas conduit providing a passageway for gas to be introduced into the blood collection tube. Included in the apparatus is insertion of the dual conduit into the blood collection tube, turning the tube away from a vertical, upright orientation, connecting and disconnecting the gas passageway from a gas supply, displacing a volume of gas through the gas passageway, and controlling the operation of the apparatus. A method is also disclosed involving insertion of a dual conduit into a closed blood collection tube, connecting a gas supply to a gas conduit of the dual conduit, rotating the tube away from a vertical, upright orientation, introducing a volume of gas corresponding to a signal into the blood collection tube, receiving a predetermined volume of liquid from the blood collection tube, and physically disconnecting the gas supply from the gas passageway.

U.S. Pat. No. 5,413,246 discloses a disposable apparatus to dispense an amount of liquid from a closed container using a stopper piercing means to access the interior of a closed blood collection tube, a gas passage means to allow a metered amount of gas to be forced into the blood collection tube, and a liquid passage means to allow fluid to be dispensed from the tube in proportion to the amount of gas forced into the tube. Also disclosed is a machine which uses a disposable apparatus to dispense liquid from a sequence of closed blood collection tubes in an automated manner. Liquid contained within a blood collection tube is dispensed from the tube by a control means according to signals indicative of the amount of liquid within the tube and the amount of liquid that is desired to be dispensed. A manually operated machine that uses the disposable apparatus to dispense a sample of liquid from a closed blood collection tube is also described.

U.S. Pat. No. 5,499,545 is a method for improving measurement accuracy by eliminating the influence of changes in the atmospheric and internal pressures on the quantity of a liquid absorbed or discharged. A pipetting device inducts a specified quantity of liquid into a tip portion or discharges a specified quantity of liquid from the tip portion by controlling the pressure inside a cylinder portion including a cylinder and a piston. A control target value for the quantity of the liquid to be absorbed or discharged from a command portion and information from an atmospheric pressure measurement portion and a pressure sensor for detecting the internal pressure of the cylinder are sent to a correction calculation portion which in turn performs correction calculation based on measured data on the atmospheric and internal pressures and data on the shapes of the cylinder and tip portion to obtain the distance to be traveled by the piston so that the control target value form the command portion is met. A control portion controls a motor which drives the piston in accordance with information on the distance to be traveled by the piston from the correction calculation portion.

Accordingly, from a study of the different approaches taken in the prior art to the problems presented by the necessity for efficiently extracting a known amount of liquid from a closed container, taken with the challenge of ensuring that the extracted sample be free of disruptive nonhomogenities, there remains a need for an improved approach to provide liquid samples to an automated clinical analyzer without introducing complex control mechanisms and without unduly adding to the resources required.

BRIEF SUMMARY OF THE INVENTION

Many of these disadvantages within the prior art are overcome by using the apparatus and methods of this invention. The automated liquid sampling system employs a penetrating cannula having an elongate passage therethrough and a second passage such as a channel or groove-shaped orfice extending partially along the outermost surface thereof to produce a temporary opening in the closure of a closed liquid sample container supported within a chamber, which may be telescoping. Positive air pressure is generated within the chamber as the chamber is closed, and a portion of the telescoping chamber or another moving member forces the cannula to increasingly penetrate the closure. A valve is opened and closed or a pump may be controlled to maintain a positive pressure inside the chamber within predetermined limits. In an operating position, the cannula is inserted into the sample container a distance sufficient to establish fluid communication both between the chamber and the interior of the sample container by means of the partial groove or channel and between the interior of the sample container and an external sample receptacle by means of the elongate passage. Positive air pressure differential transmitted from the chamber through the groove to the interior of the sample container forces liquid sample to be dispensed from within the interior of the sample container through the elongate passage into the external receptacle. By monitoring the differential pressure within the chamber, a precisely known quantity of sample is extracted. Opening a valve to produce equilibrated pressures between the interior and exterior of the sample container stops dispensation of additional liquid sample. When dispensing of the desired amount of sample is completed, the sample container is forced over the cannula a sufficient distance to position the sample container closure beyond the partial groove or channel thus preventing further fluid communication between the chamber and the interior of the sample container. With minimal expense of manufacture and assembly, the present invention produces the requisite actions to temporarily open the closure of a sample container, establish access to the inside of the container, and extract an accurately controlled quantity of liquid sample.

BRIEF DESCRIPTION OF THE DRAWINGS

The invention will be more fully understood from the following detailed description thereof taken in connection with the accompanying drawings which form a part of this application and in which:

FIG. 2 is a cross-sectional view showing a sample container positioned within a telescoping chamber and in penetrating alignment with the penetrating cannula of the present invention;

FIG. 3 is a cross-sectional view showing a sample container positioned within a telescoping chamber and in a first pre-operating position with the penetrating cannula of the present invention;

FIG. 5 is a cross-sectional view showing a sample container positioned within a telescoping chamber and in an operating position with the penetrating cannula of the present invention;

FIG. 6 is a cross-sectional view showing a sample container positioned within a telescoping chamber and in a post-operating position with the penetrating cannula of the present invention;

DETAILED DESCRIPTION OF THE INVENTION

Figure 1:
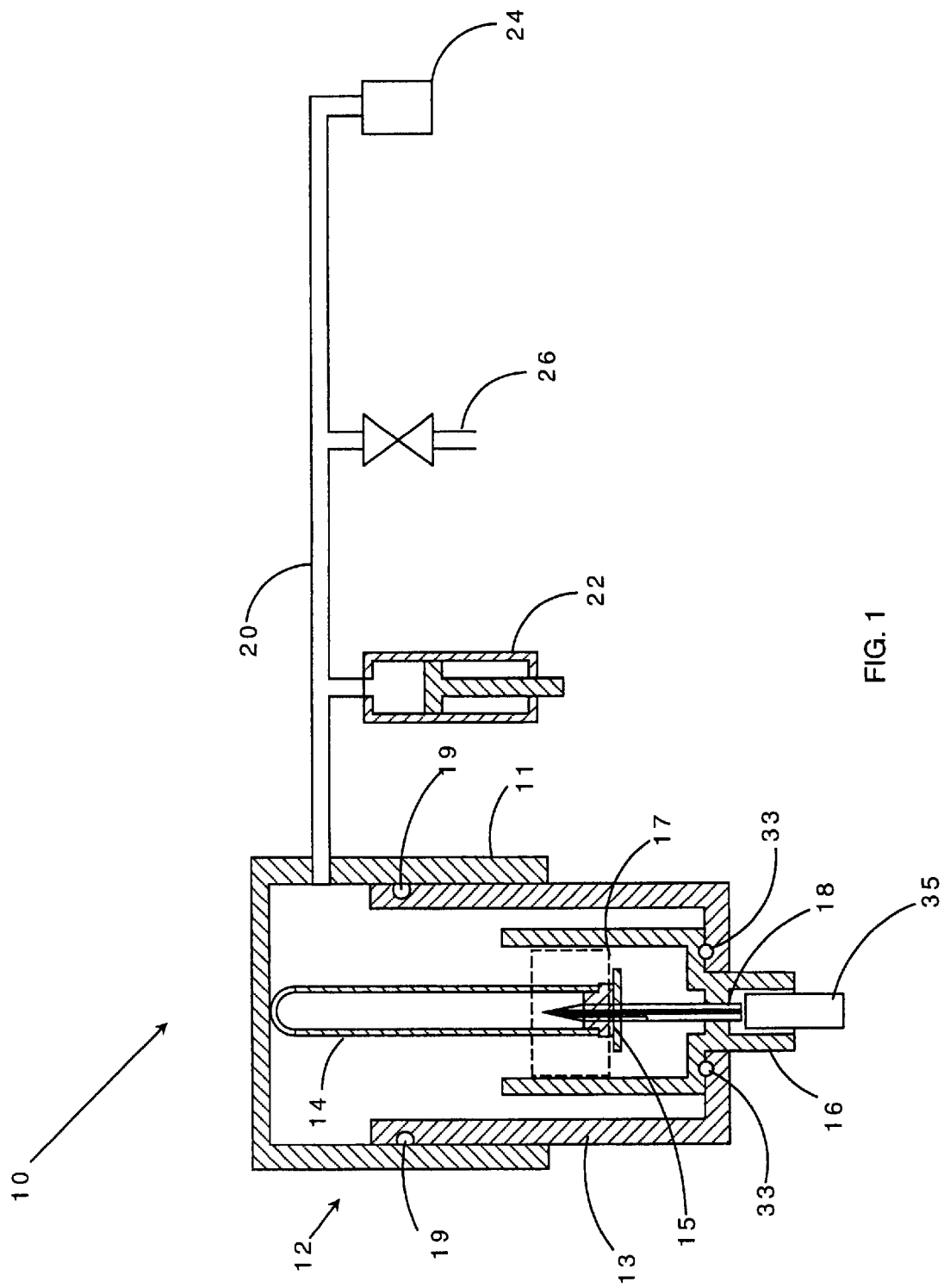
FIG. 1 is a schematic view of an automated liquid sampling system in which the present invention may be used to advantage.

FIG. 1 shows schematically the elements of an automatic liquid sampling system 10 comprising a telescoping chamber 12 comprising an uppermost portion 11 adapted by conventional motorized means (not shown) to be moveable between fully open and fully closed positions relative to a lowermost portion 13, the uppermost portion 11 and lowermost portion 13 being sized to engage the exterior surface of the lowermost within the innermost surface of the uppermost portion. A seal 19 is disposed within telescoping chamber 12 to achieve a pressure-tight relationship between the uppermost portion 11 and lowermost portion 13. In the fully open position, a liquid sample container 14 containing liquid sample to be extracted from container 14 is placed in a resting position within the upper confines of a cupping member 16 so that the closure 15 of the sample container is contacted without penetration thereof by a penetrating cannula 18. A vacuum or pressure line 20 maintains the interior of the telescoping chamber 12 in pneumatic communication with a conventional positive pressure or vacuum pump 22, a pressure measuring transducer 24, and a valve 26 within line 20 adapted to quickly open the line 20 and thereby the interior of the chamber 12 to atmospheric environment.

FIG. 2 is an enlarged view of telescoping chamber 12 and the liquid sample container 14 shown in a resting position within the upper confines of cupping member 16 so that the closure 15 of the sample container 14 rests upon the penetrating cannula 18 without penetration thereof. The inside dimension of cupping member 16 is adjusted to loosely mate with plastic enclosure 17 (shown in dashed lines for clarity), the enclosure 17 designed to facilitate operator handling and to protect the closure 15 and sample container 14. Penetrating cannula 18 is formed within the base of cupping member 16 and has a sharp, penetrating section 30 at that end of the cannula 18 aligned with and contacting the liquid sample container 14. The end of cannula 18 opposite to section 30 is located outside the telescoping chamber 12. An elongate passage 32 extends axially through cannula 18 and a groove shaped orfice 34 axially extends a partial length along the outermost surface thereof. As seen in FIG. 2, elongate passage 32 establishes fluid communication between the interior and exterior of chamber 12 while partial channel 34 is located entirely within chamber 12. The length of orfice or channel 34 is made to be at least as great as the axial length of closure 15. In an alternate embodiment, both elongate passage 32 and partial channel 34 may establishes fluid communication between the interior and exterior of chamber 12, partial channel 34 being connected to a source of vacuum or pressure so as to eliminate the necessity for pressurized chamber 12.

FIG. 3 shows chamber 12 in an pre-operating position in which the uppermost portion 11 and lowermost portions 13 of the chamber 12 have been telescopically engaged a sufficient distance to force the penetrating cannula 18 to penetrate partially through closure 15. As explained in greater detail hereinafter, this initial penetration of closure 15 may displace closure 15 an amount sufficient to generate a small positive pressure within sample container 14.

Figure 4:
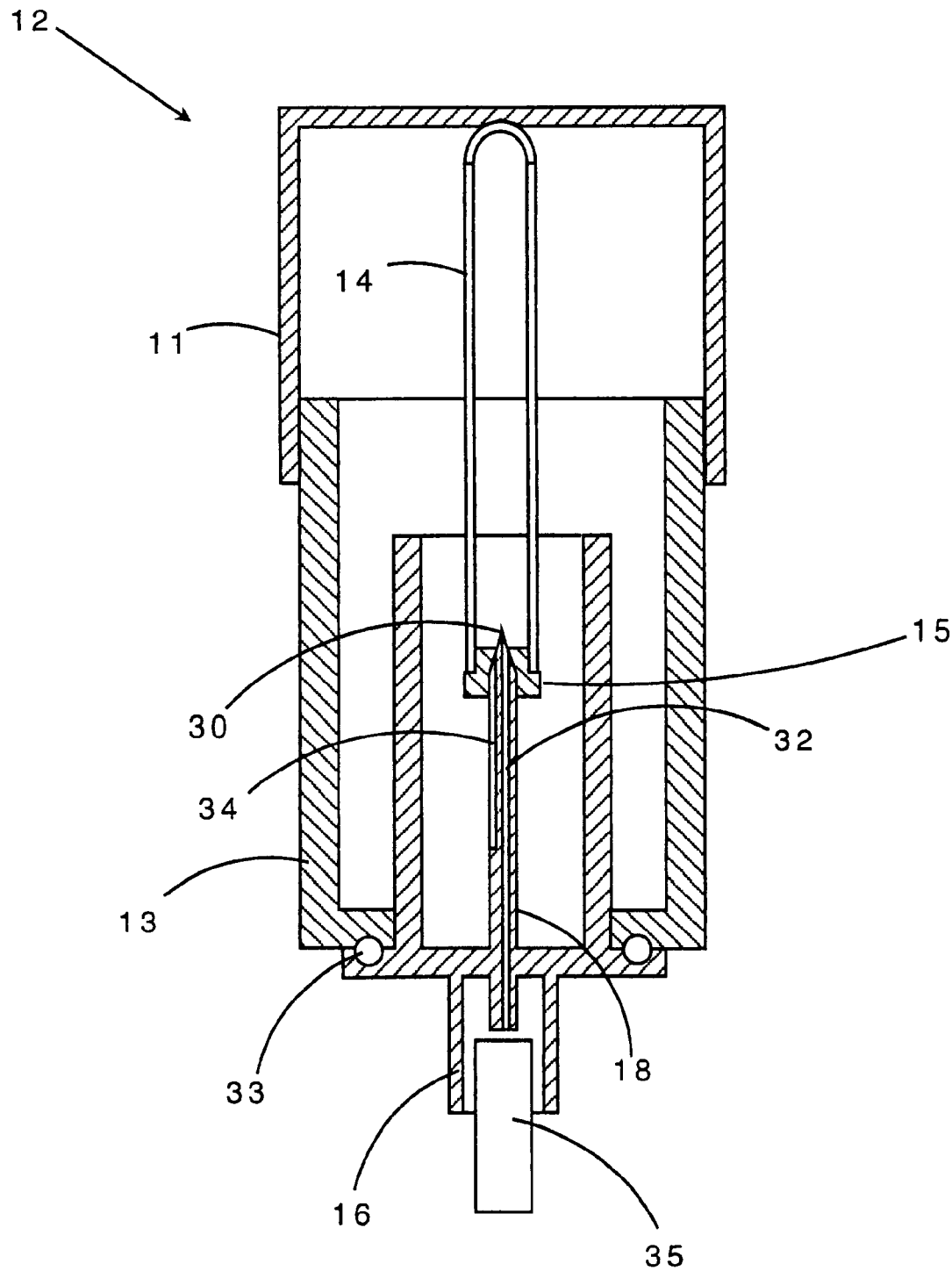
FIG. 4 is a cross-sectional view showing a sample container positioned within a telescoping chamber and in a second pre-operating position with the penetrating cannula of the present invention.

FIG. 4 shows chamber 12 in an pre-operating position in which the uppermost portion 11 and lowermost portions 13 of the chamber 12 have been telescopically engaged a sufficient distance to force the penetrating cannula 18 to penetrate fully through closure 15 so that passage 32 establishes fluid communication between the interior of the sample container 14 and exterior of chamber 12. In this pre-operating position, a small amount of liquid sample may be expelled from within sample container 14 through passage 32 due to any positive pressure within sample container 14; air may be drawn into container 14 from the external environment and atmospheric pressure equilibrium will be established therebetween.

FIG. 5 shows chamber 12 in an operating position in which the uppermost portion 11 and lowermost portions 13 of the chamber 12 have been telescopically engaged a sufficient distance to force the penetrating cannula 18 to penetrate further through closure 15 so that channel 34 establishes fluid communication between the interior of sample container 14 and the interior of chamber 12. Removal of a desired predetermined amount of sample from within container 14 is achieved as explained hereinafter in this operating position.

FIG. 6 shows chamber 12 in an post-operating position in which the uppermost portion 11 and lowermost portions 13 of the chamber 12 have been fully engaged forcing the penetrating cannula 18 to penetrate fully through closure 15 to contact the base of cupping member 16 so that groove 34 is fully within sample container 14. Upon opening of telescoping chamber 12, sample container 14 may be safely discarded by an operator without danger of additional liquid sample flowing out of passage 32 as it is secured to cupping member 16 by the impaling cannula 18.

Figure 7:
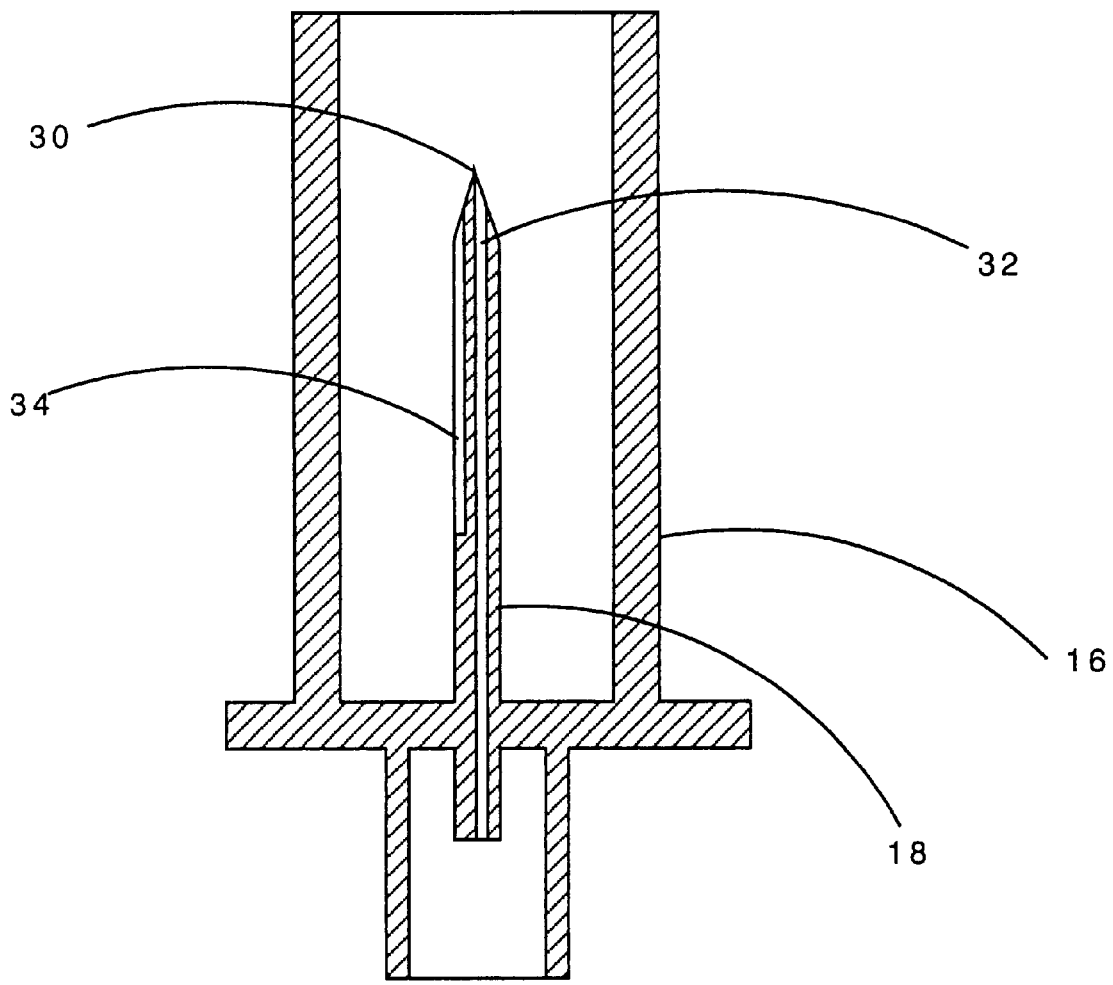
FIG. 7 is an enlarged cross-sectional view of a penetrating cannula illustrative of the present invention; and, FIG. 8 is a schematic representation of a time sequence of events exemplary of the present invention.

FIG. 7 is an enlarged view of penetrating cannula 18 to better illustrate elongate passage 32 extending axially therethrough and channel 34 axially extending a partial length along the outermost surface thereof.

Figure 8:
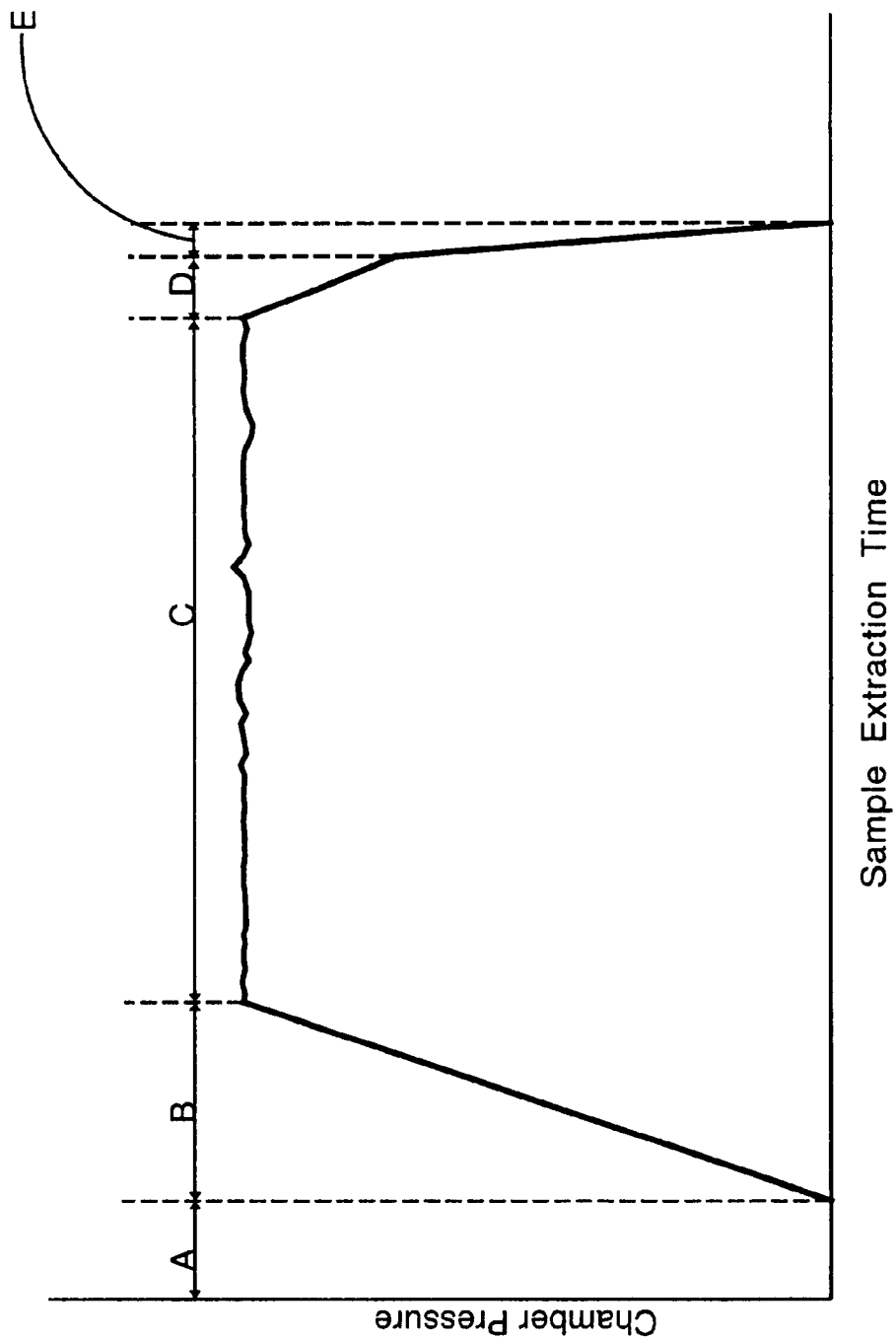

In accordance with the present invention and as illustrated in FIG. 8, a precisely controlled amount of liquid sample may be removed from a closed sample container 14 by monitoring the pressure within chamber 12 and opening valve 26 to atmospheric conditions. FIG. 7 shows the pressure as measured within chamber 14 by transducer 26 as a function of a time sequence of events A–E, in which:

A: an initial time period during which a sample container 14 is placed within chamber 12 with valve 26 open to ambient pressure. Chamber 12 is closed by telescoping upper portion 11 downwards over lower portion 13. During this period, closure 15 is resting in a non-penetrating position atop cannula 18, as shown in FIG. 2.

B: a first pre-operating time period after chamber 12 is closed during which valve 26 is closed and chamber 12 is further closed so that an increasing positive pressure is generated within chamber 12. During this period, closure 15 is increasingly penetrated by cannula 18, as shown in the first pre-operating position illustrated in FIG. 3. No liquid sample flows out of cannula 18.

C: a second pre-operating time period after chamber 12 is closed during which valve 26 is closed and chamber 12 is closed to the extent that a predetermined positive pressure is generated within chamber 12. During this period, closure 15 is penetrated by cannula 18, as shown in the second pre-operating position illustrated in FIG. 4, to a distance that groove 34 has not reached the interior of sample container 14. In this second pre-operating position, the pressure measured by transducer 24 is maintained within chamber 12 in the range of about 0.8 to 1.1 psi by operating valve 26, that is opening and/or closing valve 26 or compensated by appropriate movement of a pumping means, for example by controlling the action of a syringe pump. No liquid sample flows out of cannula 18.

D: an operating time period during which closure 15 is penetrated by cannula 18, as shown in the operating position illustrated in FIG. 5. so that groove 34 has reached the interior of sample container 14. An open path is created by groove 34 between the interior of telescoping chamber 12 and the interior of sample container 14 so that a flow of air enters into the sample container 14. The flow of air into the interior of sample container 14 forces liquid to flow through the passage 32 and into a receptacle 35 positioned beneath the cupping member 16. As seen in FIG. 8, the positive pressure conditions within chamber 12 decrease rapidly during time period D. As shown in TABLE 1 below, it has been discovered that the decrease in pressure within chamber 12 is related to the volume of liquid sample forced from within the sample container 14. This discovery permits a desired amount of liquid to be extracted from within container 14 by allowing sample to be forced from the container until the pressure within chamber 12 reaches a predetermined level.

TABLE 1

| Total Pressure Change | Amount of Liquid Transferred from Container 14 |
| --- | --- |
| −0.37 psi | 1.7 mL |
| −0.44 psi | 2.2 mL |
| −0.49 psi | 2.4 mL |

Once the above relationship between change in pressure within the sample container and the amount of liquid extracted has been established for a given tube size, cannula and chamber, it becomes possible to accurately extract a desired volume of liquid from within similar containers by monitoring air pressure within the interior of the chamber 12 using a device like transducer 24 and opening a device like value 26 to atmospheric pressure whenever the total pressure change indicated by transducer 26 has reached the level predetermined to correspond to the desired volume of liquid, for example as shown in TABLE 1. An advantage of the present method is elimination of sample volume errors that may occur if liquid sample is extracted from a closed sample container without equilibration of pressure between the interior and exterior of the sample container 14.

In an exemplary embodiment, designed to remove quantities of body fluid like serum or urine in the range of 1.0 to 4.0 ml from a 5 ml sample tube like a Vacutainer® tube containing lithium heparin available from Beckton Dickinson, cupping member 16 is molded from a polymeric material like Cyrano® polyethylene with the portion containing cannula 18 having dimensions of about 2 cm outer diameter, 5 cm depth and wall thickness about 0.1 cm. Cannula 18 has height about 4 cm and diameter 0.4 cm with passage 32 about 0.09 cm diameter extending the length of the cannula and groove 34 about 0.06 cm extending a length about 1.2 cm originating about 0.002 cm from the tip of cannula 18. Lower portion 13 is also molded from Cyrano® polyethylene into a 2.5 cm inner diameter cylinder-like member with wall thickness about 0.3 cm and height about 7 cm; upper portion 11 is about 5 cm in height and may be formed as a block-like member having a closed bore with its inner surface vacuum sealed to the outer surface of lower portion 13 with a conventional elastomeric o-ring seal. A stepper motor, for example a Vexta® motor available from Oriental Motor, is adapted to telescope the upper portion 11 over lower portion in a series of 0.002 cm steps at a rate of about 5 steps per second. Cupping member 16 may be pressure sealed to lower portion 13 using a conventional elastomeric o-ring or flat seal.

When operated in the arrangement as shown in FIG. 1, an open 0.1 cm diameter pressure line 20 connects the interior of telescoping chamber 12 to a syringe-action pressure pump 22, like those available from Klone, a pressure measuring transducer 24, like those available from SenSym, and a diaphragm valve 26, like those available from General Valve to quickly open line 20 and thereby bring the interior of the chamber 12 to atmospheric environment. In operation, pressures within telescoping chamber 12 like those in TABLE 2 below have been found to provide liquid sample volume in the range of 1–4 ml with a standard deviation of about 6%.

TABLE 2

| Operation | Pressures | Time Interval | Operation |
|---|---|---|---|
| A | 0 psi | 2 sec | close chamber 12 |
| B | 0–0.9 psi | 17 sec | cannula begins penetration of closure 15 |
| C | 0.9 ± 2% psi | 47 sec | valve 26 and pump 22 maintain chamber pressure as cannula penetration continues; passage 32 enters interior of tube 14 |
| D | 0.9–0.5 psi | 0.5 sec | groove 34 enters interior of tube 14 and liquid is forced from tube 14 through passage 34 into receptacle 35 |
| E | 0.5–0 psi | 2.5 sec | chamber 12 is fully closed; cannula 18 fully penetrated closure 15 and the extraction is complete. |

It is to be understood that the embodiments of the invention disclosed herein are illustrative of the principles of the invention and that other modifications may be employed which are still within the scope of the invention. For example, in one alternate exemplary embodiment, chamber 12 is maintained at a negative operating pressure, and the functions of passage 32 and channel 34 are reversed. In another alternate exemplary embodiment, passage 32 and channel 34 are both enclosed passages extending the length of the cannula with one passage used to flow fluid from within the sample container 14 to a receptacle 35 and the other passage connected to the pressure source 22, valve 26 and transducer 24 in line 20, thereby eliminating the need for enclosing the sample container 14 in chamber 12. In even another alternate exemplary embodiment, chamber 12 may be positioned on the "exit" end of cannula 18 and the sample container 14 exposed to atmospheric conditions, in which event a negative pressure would be monitored by transducer 24 and an increasing pressure would be controlled within the chamber 12 until the interior of the liquid sample container 14 was vented to the interior of the chamber 12. Additionally, pressure pump 22 may be replaced with a conventional source of vacuum or pressure acting in cooperation with another valve and pressure transducer to maintain a constant operating pressure or vacuum within chamber 12. Accordingly, the present invention is not limited to those embodiments precisely shown and described in the specification but only by the following claims.

What is claimed is:

1. A method for extracting a desired quantity of liquid from the interior of a container closed with a penetrable closure comprising the steps of:

(a) placing the container within the interior of a sealed telescoping chamber, said chamber having:

a lower portion adapted to support a cannula within the chamber and to position the penetrable closure at the cannula, and an upper portion adapted to force the penetrable closure over the cannula when the upper portion is moved over the lower portion;

(b) establishing pneumatic communication between the chamber and a pressure transducer and pressure control means;

(c) initiating penetration of the closure with the cannula by closing the telescoping chamber, said cannula having a passage extending the length of the cannula and a groove extending a partial length of the cannula;

(d) operating the pressure control means in response to the transducer so as to maintain a constant pressure range within the chamber;

(e) continuing penetration of the closure with the cannula until the groove establishes open communication between the interior of the chamber and the interior of the container, thereby forcing liquid from the tube through the passage; and, (f) opening the valve after the desired quantity of fluid has been forced from the container.

2. The method of claim 1 wherein the chamber is a sealed telescoping chamber and initiating penetration of the closure with the cannula comprises compressing the telescoping chamber.

3. The method of claim 1 wherein the pressure control means comprises a valve or a pump.

4. The method of claim 1 wherein the pressure control means comprises a valve and a pump.

5. The method of claim 1 wherein the cannula is integral with and extends upwards from the bottom of a cupping member sized to mate with the container.

6. The method of claim 3 wherein the cupping member is sealably mounted within an opening in the chamber.

7. The method of claim 4 wherein the cupping member is disposable.

8. The method of claim 1 wherein the container is a tube containing a body fluid.

9. The method of claim 1 wherein the desired quantity of fluid is in the range of 1–4 ml.

10. The method of claim 2 wherein compressing the telescoping chamber comprises driving an upper portion of the chamber over a lower portion of the chamber using a motor.

11. A method for extracting a desired quantity of liquid from the interior of a container closed with a penetrable closure, the container disposed within the interior of a chamber, the chamber in pneumatic communication with a pressure transducer, and pressure control means, the method comprising the steps of:

initiating penetration of the closure with a cannula having a passage extending the length of the cannula and a groove extending a partial length of the cannula;

operating the pressure control means in response to the transducer so as to maintain a relatively constant pressure range within the chamber;

continuing penetration of the closure with the cannula until the groove establishes open communication between the interior of the chamber and the interior of the container, thereby forcing liquid from the tube through the passage; and, opening the valve after the desired quantity of fluid has been forced from the container.

12. An apparatus for extracting a desired quantity of liquid from the interior of a container closed with a penetrable closure comprising:

a sealable chamber;

means to maintain a constant pressure within the chamber;

a cannula disposed within the chamber and having a passage extending from the tip of the cannula the length of the cannula to the exterior of the chamber and a groove extending from near the tip of the cannula a partial length of the cannula; and, means to compress the chamber so that the tip of the cannula is driven through the closure, whereby liquid is forced from the container through the passage to the exterior of the chamber when the groove establishes communication between the interior of the chamber and the interior of the container.

13. An apparatus for extracting a desired quantity of liquid from the interior of a container closed with a penetrable closure comprising:

a sealed telescoping chamber having:
      a lower portion adapted to support a cannula within the chamber and to position the penetrable closure at the cannula, and
      an upper portion adapted to force the penetrable closure over the cannula when the upper portion is moved over the lower portion;

means to maintain a constant pressure within the chamber;

wherein the cannula is disposed within the chamber and has a passage extending from the tip of the cannula the length of the cannula to the exterior of the chamber and a groove extending from near the tip of the cannula a partial length of the cannula; and, means to compress the chamber so that the tip of the cannula is driven through the closure, whereby liquid is forced from the container through the passage to the exterior of the chamber when the groove establishes communication between the interior of the chamber and the interior of the container.

14. The apparatus of claim 13 wherein the cannula is integral with and extends upwards from the bottom of a cupping member sized to mate with the container.

15. The apparatus of claim 14 wherein the cupping member is sealably mounted within an opening in the chamber.

16. The apparatus of claim 15 wherein the cupping member is disposable.

17. The apparatus of claim 13 wherein the container is a tube containing a body fluid.

18. The apparatus of claim 13 wherein the desired quantity of fluid is in the range of 1 to 4 ml.

19. The apparatus of claim 13 wherein the means to maintain a constant pressure within the chamber comprises a pneumatic line connected to the chamber, a pressure transducer, a valve and a pump.

* * * * *